United States Patent [19]

Tvrtkovic-Sahin et al.

[11] Patent Number: Plant 7,401

[45] Date of Patent: Dec. 18, 1990

[54] ASTER PLANT NAMED PINK BUTTERFLY

[76] Inventors: Zelimir K. Tvrtkovic-Sahin, Barnsteenstraat 24,, 2403 BZ Alphen aan den Rijn; Petrus J. Akerboom, Paradijsweg 61, 2461 TL, Ter Aar, both of Netherlands

[21] Appl. No.: 378,179

[22] Filed: Jul. 11, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

An Aster plant named Pink Butterfly particularly characterized by its cupped capitulum form; daisy capitulum type; light pink ray floret color; diameter across face of capitulum of 29 to 32 mm at maturity; strong, well branched flower stems; and many capitula per inflorescence on short pedicels.

1 Drawing Sheet

1

The present invention comprises a new and distinct cultivar of Aster plant, hereinafter referred to by the cultivar name Pink Butterfly.

Pink Butterfly is a product of a planned breeding program which had the objective of creating new perennial Aster cultivars for year-round commercial production and having well branched flower stems, good flower size, a nice light pink color, good flower form, and a good lasting quality of the cut flowers. Such traits in combination were not present in previously available commercial cultivars.

Pink Butterfly was originated from a hybridization made by the inventors K. Sahin and P. Akerboom in a controlled breeding program in Ter Aar, The Netherlands, in 1985. The female parent of Pink Butterly was *Aster pringlei* c.v. Monte Casino. The male parent was an unnamed *Aster novi-belgii* seedling.

Pink Butterfly was discovered and selected as one flowering plant within the progeny of the stated parentage by the joint inventors K. Sahin and P. Akerboom on Sept. 2, 1986 in a controlled environment in Ter Aar, and identified as Seedling No. 85/3250.

The first act of asexual reproduction of Pink Butterfly was accomplished when vegetative cuttings were taken from the initial selection in Nov. 1986 in a controlled environment in Ter Aar, by a technician working under formulations established and supervised by K. Sahin and P. Akerboom.

Horticultural examination of selected units initiated in 1986 and 1987 has demonstrated that the unique combination of characteristics as herein disclosed for Pink Butterfly are firmly fixed and are retained through successive generations of asexual reproduction.

Pink Butterfly has not been observed under all possible environmental conditions. The phenotype may vary significantly with variations in environment such as temperature, light intensity and daylength.

The following observations, measurements and comparisons describe plants grown in Ter Aar under greenhouse conditions which approximate those generally used in commercial greenhouse practice in The Netherlands.

The following traits have been repeatedly observed and are determined to be basic characteristics of Pink Butterfly, which, in combination, distinguish this Aster as a new and distinct cultivar:

1. Cupped capitulum form.

2

2. Daisy capitulum type.
3. Light pink ray floret color.
4. Diameter across face of capitulum of 29 to 32 mm at maturity.
5. Strong, well branched flower stems.
6. Many capitula per inflorescence on short pedicels.

The accompanying photographic drawing shows typical inflorescence of Pink Butterfly, with the colors being as nearly true as possible with illustrations of this type. The color photograph is a front perspective view of Pink Butterfly shown grown as a single stem cut spray Aster.

Of the commercial cultivars known to the inventors, the most similar in comparison to Pink Butterfly is the female parent Monte Casino. Reference is made to attached Chart A, which compares certain characteristics of Pink Butterfly to the same characteristics of Monte Casino.

In comparison to Monte Casino, Pink Butterfly has stronger flower stems, better branching, more capitula per inflorescence, larger flowers, and better lasting quality of the cut flowers. With regard to the last mentioned characteristic, when grown under similar conditions, the blossoms of Pink Butterfly will last 2–3 days longer than the flowers of Monte Casino. In addition, the ray floret color of Pink Butterfly is light pink, while the ray floret color of Monte Casino is white. Similar traits are capitulum form and type, spray formation and photoperiodic light reaction.

In the following description color references are made to The Royal Horticultural Society Colour Chart. The color values were determined between 14:00 and 15:00 hours on Oct. 20, 1987 at Alphen aan den Rijn, The Netherlands.

Classification:

*Botanical.*—*Aster pringlei* × *novi-belgii* cv Pink Butterfly.

*Commercial.*—Small daisy-like spray Aster perennial.

INFLORESCENCE

A. Capitulum:

*Form.*—Cupped.

*Type.*—Daisy.

*Diameter across face.*—29–32 mm.

*Arrangement.*—Raceme inflorescence.

B. Corolla of ray florets:

*Color (general tonality from a distance of three meters).*—Light pink.

*Color (upper surface).*—Closest to 69A.

*Color (under surface).*—Closest to 69A.

*Shape of floret.*—Narrow, oblong, straight.

*Size of floret.*—15 mm long×2 mm wide.

*Number of ray florets.*—23–25.

C. Corolla of disc florets:

*Color (mature).*—Closest to 1C to 1D.

*Color (immature)* Closest to 1C to 1D.

*Diameter of disc.*—7–8 mm.

D. Reproductive organs:

*Androecium.*—Present on disc florets only; no pollen.

*Gynoecium.*—Present on both ray and disc florets.

PLANT

A. General appearance:

*Height.*—Medium to tall; depends on light availability. Under continuous long days it can grow up to 2 meters tall medium to heavy branching.

B. Foliage:

*Color.*—147A to 147B.

*Shape.*—Oblanceolate and linear, with occasional downward reflexing at the tip.

*Size.*—110–117 mm long×8–9 mm wide.

*Length.*—Short to medium; width medium to broad.

*Margin.*—Entire.

*Arrangement.*—Alternate, with angle acute.

CHART A
COMPARISON OF PINK BUTTERFLY AND MONTE CASINO

| | Pink Butterfly | Monte Casino |
|---|---|---|
| Ray Floret Color | Light pink | White |
| Capitulum Form and Type | Cupped daisy | Cupped daisy |
| Spray formation | Compound | Compound |
| Pedicels | 7–12 mm long | 7 mm long |
| Diameter across face of capitulum | 29–32 mm | 20–22 mm |
| Number of ray florets | 23–25 | 27 |

Comparisons made on plants grown as single stem spray Asters in Ter Aar, The Netherlands

We claim:

1. A new and distinct Aster plant named Pink Butterfly, as described and illustrated.

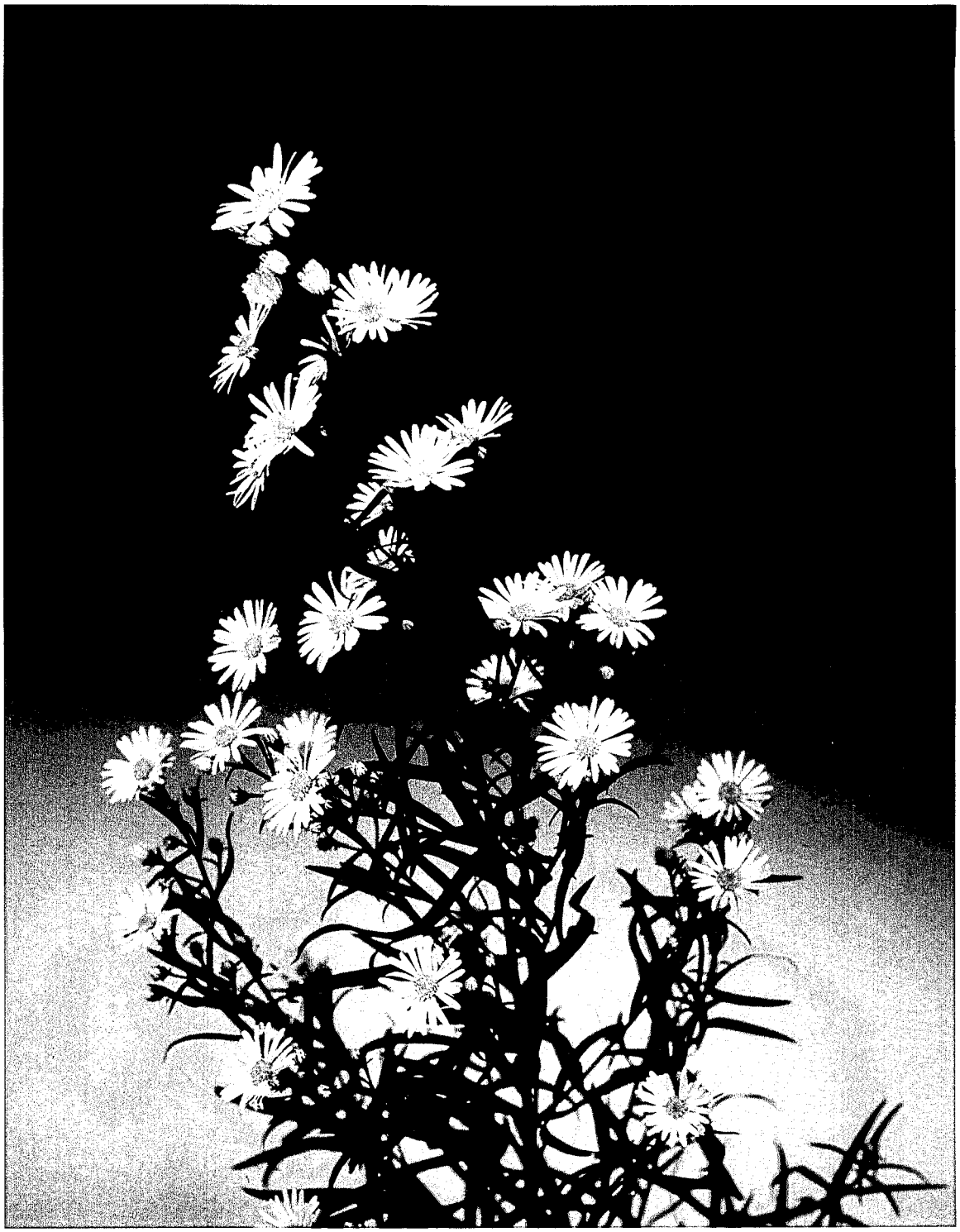

* * * * *